United States Patent [19]

Telschow

[11] Patent Number: 4,696,774
[45] Date of Patent: Sep. 29, 1987

[54] DECOLORIZING ARYLSULFONYL HALIDES

[75] Inventor: Jeffrey E. Telschow, Tarrytown, N.Y.

[73] Assignee: Stauffer Chemical Company, Westport, Conn.

[21] Appl. No.: 843,408

[22] Filed: Mar. 24, 1986

[51] Int. Cl.$^4$ .............................................. C07C 143/00
[52] U.S. Cl. ................................. 260/543 R; 260/708
[58] Field of Search .............................. 260/543 R, 708

[56] References Cited

U.S. PATENT DOCUMENTS

| | | | |
|---|---|---|---|
| 3,644,515 | 2/1972 | Suzuki | 260/543 R |
| 3,795,705 | 3/1974 | Chan | 260/543 R |
| 4,105,692 | 8/1978 | Blank | 260/543 R |

OTHER PUBLICATIONS

Mitsui Toatsu Chem. Inc. *Derwent Abstract* 44761 D/25 *J56046-860 Japanese Patent 123,124 dated Apr. 28, 1981).

*Hackh's Chemical Dictionary* 4th Ed. (1969) McGraw Hill, Publ. pp. 200 and 481.

Mellor, J. W. *Inorganic and Theoretical Chemistry,* vol. X (1949) Longman, Green and Co., Publs. pp. 641–642.

Kirk–Othmer *Encyclopedia of Chemical Technology* 2nd Ed. vol. 19, pp. 391–395, vol. 4, p. 150.

Poshkus, A. C. et al. *J. Am. Chem. Soc., vol. 80 (1958) pp. 5022–5027.*

Evans, Alwyn G. et al. *Chemical Abstracts,* vol. 42 (1948) #4082i & 4083a.

*Primary Examiner*—Paul J. Killos
*Assistant Examiner*—L. Hendriksen
*Attorney, Agent, or Firm*—Hensley M. Flash

[57] ABSTRACT

There is disclosed a process for decolorizing arylsulfonyl halides. The disclosed process decolorizes arylsulfonyl halides derived from the reaction of an arylsulfonic acid with a sulfur halide and a corresponding halogen. The resulting arylsulfonyl halide is contacted with a decolorizing agent and thereafter optionally dstilled. The decolorizing agent can be an oxidizing agent, for example, hydrogen peroxide, sodium hypochlorite, potassium permanganate, chlorine, nitric acid, and air in the presence of platinum on charcoal catalyst. The decolorizing agent can also be a reducing agent, e.g., dimethyl phosphite, trimethyl phosphite, triphenyl phosphite, hydrogen sulfide, sodium hypophosphite and red phosphorus. Additionally, the decolorizing agent can be a compound having at least one alkene linkage, e.g., polybutadiene, $C_{14}$–$C_{30}$ alpha-olefins, and unsaturated vegetable oils.

35 Claims, No Drawings

DECOLORIZING ARYLSULFONYL HALIDES

FIELD OF THE INVENTION

The present invention relates to a process for decolorizing arylsulfonyl halides and, in particular, to decolorizing arylsulfonyl halides derived from the reaction of an arylsulfonic acid with a sulfur halide and the corresponding halogen.

BACKGROUND OF THE INVENTION

Arylsulfonyl halides, such as, for example, benzenesulfonyl chloride, are particularly useful as intermediates in the manufacture of certain biologically active compounds and as polymer plasticizers. For example, benzenesulfonyl chlorides can be reacted with primary or secondary amines to produce certain arylsulfonamides such as, for example, N-(beta-0,0-diisopropyldithiophosphorylethyl) benzenesulfonamide and N-butyl benzenesulfonamide, a nylon plasticizer.

These arylsulfonyl halides can be produced by many methods. For instance, a commonly employed procedure is the reaction of an arylsulfonic acid with either thionyl chloride or phosphorus pentachloride. Other processes include the reaction of an arylsulfonic acid with thionyl chloride in the presence of a sulfonating agent (U.S. Pat. No. 4,105,692), and the reaction of an arylsulfonic acid with a carbonyl halide in the presence of dimethylformamide and a tertiary amine (U.S. Pat. No. 3,795,705). In Yet another method, arylsulfonic acid is reacted with a sulfur monohalide in the presence of excess halogen. This latter method is especially useful in the production of benzenesulfonyl chloride wherein benzenesulfonic acid, sulfur monochloride and chlorine are reacted to produce benzenesulfonyl chloride. In this process described immediately above, the arylsulfonyl halides produced can be removed by distillation from the reaction mixture. However, the distilled arylsulfonyl halide product is usually discolored by the presence of impurities and can be almost black in color. It would be advantageous from a customer's viewpoint to treat the arylsulfonyl halide with various decolorizing agents to achieve a pale yellow to colorless product of higher purity.

SUMMARY OF THE INVENTION

In accordance with the present invention, there is disclosed a process for decolorizing an arylsulfonyl halide derived from the reaction of an arylsulfonic acid with a sulfur halide and the corresponding halogen comprising contacting the arylsulfonyl halide with a decolorizing agent, and thereafter optionally distilling the arylsulfonyl halide. The decolorizing agent can be an oxidizing agent selected from the group consisting of hydrogen peroxide, sodium hypochlorite, potassium permanganate, chlorine, nitric acid, and air in the presence of platinum on charcoal catalyst. The decolorizing agent can also be a reducing agent selected from the group consisting of dimethyl phosphite, trimethyl phosphite, triphenyl phosphite, hydrogen sulfide, sodium hypophosphite and red phosphorus. The decolorizing agent can also be a compound having at least one alkene linkage selected from the group consisting of polybutadiene, $C_{14}$ to $C_{30}$ alpha-olefins, and unsaturated vegetable oils. In a preferred embodiment of this invention the arylsulfonic acid is benzenesulfonic acid and a preferred arylsulfonyl halide is benzenesulfonyl chloride (BSC).

DETAILED DESCRIPTION OF THE INVENTION

The present invention is directed to a process for decolorizing arylsulfonyl halides derived from the reaction of an arylsulfonic acid with a sulfur halide and the corresponding halogen. These arylsulfonic halides are derived from an arylsulfonic acid of the general formula:

$$ArSO_3H$$

wherein Ar represents an aryl moiety which includes phenyl or substituted phenyl, naphthyl or substituted naphthyl and heteroacylic aromatic compounds. The substituents on the aryl moiety include halides and particularly chlorine, bromine, fluorine, iodine, alkyl and alkenyl groups, preferably lower alkyl or lower alkenyl, aryl, nitro, cyano, alkoxy, carboalkoxy, acyloxy, acylamido, acyl, formyl, alkyl mercapto, aryl mercapto, alkylsulfinyl, arylsulfinyl, alkylsulfonyl, arylsulfonyl and alkenylsulfonyl.

The arylsulfonic acid used in the present invention can also be in the form of a metal salt represented by the formula:

$$ArSO_3M$$

wherein Ar is as defined above, and M represents an alkali or alkaline earth metal, which for reasons of cost and availability, will preferably be sodium or potassium. As used in regard to the present invention, the term "arylsulfonic acid" shall be inclusive of both the acid and salt forms thereof.

Illustrative of those sulfonic acids which can be used in the present invention, in either the form of an alkali or alkaline earth metal salt or in the free sulfonic acid form, are benzenesulfonic acid, chlorobenzenesulfonic acid, trichlorobenzenesulfonic acid, toluenesulfonic acid, 1-naphthalenesulfonic acid, 2-naphthalenesulfonic acid, 2-anthraquinonesulfonic acid, 4-pyridinesulfonic acid, 2-thiophenesulfonic acid, p-methoxybenzenesulfonic acid, p-carbomethoxybenzenesulfonic acid, p-acetoxybenzenesulfonic acid, p-acetylbenzenesulfonic acid, m-acetylbenzenesulfonic acid, o-acetylbenzenesulfonic acid, p-formylbenzenesulfonic acid, m-formylbenzenesulfonic acid, p-cyanobenzenesulfonic acid, p-acetylaminobenzenesulfonic acid, p-nitrobenzenesulfonic acid, p-methylmercaptobenzenesulfonic acid, p-phenylmercaptobenzenesulfonic acid, p-phenylsulfonylbenzenesulfonic acid and the like.

To produce the arylsulfonyl halide, the arylsulfonic acid described above is reacted with a halogen-supplying reagent which can be represented by any of the formulas:

$$SOX_2, SO_2X_2, PX_3, PX_5, POX_3, COX_2, SX_2 \text{ or } S_2X_2$$

wherein X is a halogen.

Exemplary halogen-supplying reagents represented by the above formulas can include thionyl chloride, sulfuryl chloride, phosphorus trichloride, phosphorus pentachloride, phosphorus oxychloride, sulfur dichloride and sulfur monochloride as well as the bromine analogues thereof. In a preferred embodiment of the present invention, the arylsulfonic acid is halogenated using a sulfur halide in the presence of halogen. The remaining description of the invention will be discussed in relation to the reaction of an arylsulfonic acid with a sulfur halide and halogen to produce an arylsulfonyl halide although it is to be understood that the present discussion applies equally to an arylsulfonyl halide produced by any of the previously discussed methods.

In a preferred embodiment of the present invention, an arylsulfonic acid is reacted with a sulfur monohalide in the presence of halogen to produce the desired arylsulfonyl halide. This reaction can be expressed as follows:

$$4ArSO_3H + S_2X_2 + 3X_2 \rightarrow 4ArSO_2X + 4HX + 2SO_2$$

The above reaction can also be treated as a series of separate reactions. In one series of reactions, the halogen reacts with sulfur or the sulfur halide, a reaction whose chemistry is described by the following reactions:

(a) $2S + X_2 \rightarrow S_2X_2$     (i)

(b) $S_2X_2 + X_2 \rightleftharpoons 2SX_2$     (ii)

(c) $SX_2 + X_2 \rightleftharpoons SX_4$     (iii)

(d) $2ArSO_3 + 2S_2X_2 \rightarrow 2ArSO_2X + 3S + HCl$

The arylsulfonic acid can then react with either of species (i), (ii) or (iii) to produce the desired arylsulfonyl halide as exemplified by reaction (d).

The process of the present invention can also decolorize the arylsulfonyl halide prepared from the improved process described in U.S. patent application No. 824,741 titled PROCESS FOR THE PRODUCTION OF ARYLSULFONYL HALIDES filed Jan. 31, 1986 by Louis F. Bolzan and Edward D. Weil. This improved process discloses the addition of a phosphorus-containing additive, e.g. phosphorous acid, before the reaction of the arylsulfonic acid with the sulfur halide and halogen. The phosphorus-containing additive reduces the thermal instability of the residue remaining after distillation of the arylsulfonyl halide.

The reaction temperature can range from about 60° C. to about 120° C. Once the reaction is complete, the resulting arylsulfonyl halide can be distilled under normal distillation conditions. After distillation the resulting product, i.e. the arylsulfonyl halide, is usually dark in color and can be almost black. This dark colored arylsulfonyl halide is less desirable from the customer's viewpoint and contains varying levels of impurities, primarily sulfur chlorides and possibly complex low-valence organosulfur species as well. When the arylsulfonyl halide is treated with a decolorizing agent before distillation, the resulting product after distillation is much lighter in color and can even be colorless, e.g. benzenesulfonyl chloride goes from a dark color to pale yellow or colorless.

The decolorizing agents useful in this invention can be broadly classed into three groups: oxidizing agents; reducing agents; and selected compounds having at least one alkene linkage. The decolorizing agents that are oxidizing agents are selected from the group consisting of hydrogen peroxide, sodium hypochlorite, potassium permanganate, chlorine, nitric acid, and air in the presence of platinum on charcoal catalyst. The decolorizing agents that are reducing agents are selected from the group consisting of dimethyl phosphite, trimethyl phosphite, triphenyl phosphite, hydrogen sulfide, sodium hypophosphite and red phosphorus. The decolorizing agents that are compounds having at least one alkene linkage are selected from the group consisting of polybutadiene, $C_{14}$ to $C_{30}$ alpha-olefins, and unsaturated vegetable oils. Examples of suitable unsaturated vegetable oils include soybean oil, linseed oil and corn oil.

The amount of decolorizing agent used can vary, however amounts ranging from about 0.1 to 50 weight percent are useful with a preferred amount ranging from 0.5 to 10 weight percent. The decolorizing agent is admixed with the crude arylsulfonyl halide and agitated. Any aqueous layer is separated from the layer containing the arylsulfonyl halide. This separated layer can then be subjected to distillation under normal distillation conditions to yield an improved arylsulfonyl halide having a lighter color as compared to the color resulting without the use of a decolorizing agent.

Washing with plain water as a decolorizing agent will usually improve the color, e.g., BSC goes from black to Yellow. However, this color improvement is usually not sufficiently great to satisfy commercial needs. Therefore the use of the decolorizing agents of this invention is required to satisfy these needs. The results obtained from the use of these decolorizing agents range from fair to excellent as measured by APHA Color Standards, however, the particular combination of chlorine and nitric acid has been found to be particularly effective. The chlorine can be added before, after or with the nitric acid. A sequential treatment using chlorine first, followed by nitric acid is particularly preferred. Other combinations of decolorizing agents can be used, however, care must be taken to avoid combinations that react to form products injurious to the process. Additionally, various washing steps with plain water can contribute to the final purity realized, e.g., when $Cl_2/HNO_3$ combination is used, if the nitric acid is washed out before distillation, improved results can be obtained as judged by the APHA Color Standards.

The following experiments describe various embodiments of the invention. Other embodiments will be apparent to one of ordinary skill in the art from a consideration of this specification or practice of the invention disclosed herein. It is intended that the specifications and experiments be considered as exemplary only with the true scope and spirit of the invention being indicated by the claims which follow the experiments.

EXPERIMENT 1

This experiment illustrates an improved process for producing benzenesulfonyl chloride that can be decolorized by the process of this invention.

To a 1 liter flask was added 808 grams (5.1 moles) of benzenesulfonic acid and 5.7 grams of a 70 percent solution of phosphorous acid (4.0 grams phosphorous acid/1.7 grams water). Sulfur monochloride addition was started and after all the sulfur monochloride had been added, chlorine was bubbled into the reaction mixture for a period of 20 hours at 80° C. The resultant benzenesulfonyl chloride was removed by distillation.

EXPERIMENT 2

Small portions of almost black benzenesulfonyl chloride (BSC) were shaken with various agents in small test tubes. The BSC was prepared by a process similar to the one disclosed in Experiment 1. The colors of the BSC resulting after shaking were compared qualitatively. Almost no effect was observed with activated charcoal. Plain water caused the color to lighten to light yellow. Almost complete color removal was observed when either 6 weight percent hydrogen peroxide, saturated sodium bicarbonate, or 5 weight percent sodium hypochlorite were used as the decolorizing agent. The use of sodium hypochlorite gave the best results.

A 1 pint quantity of black BSC was shaken twice with small portions of sodium hypochlorite and then once with saturated sodium bicarbonate. The separated BSC layer was stripped of water under vacuum and filtered. The resulting material (97.5 weight percent recovered) was pale yellow (about 30-40 on the APHA Color Standards) and after a simple distillation was colorless. When water alone is used as the decolorizing agent the resulting BSC is pale yellow even after distillation.

EXPERIMENT 3

The following tables summarize the results obtained after contacting the BSC produced by the process of Experiment 1 with various decolorizing agents. TABLE I shows the result of the decolorization of 100 g. of BSC with 20-50 mls of an aqueous solution of an oxidizing or reducing agent. TABLE II shows the result of decolorizing the BSC using varying amounts of pure non-aqueous compounds including reducing agents and selected compounds having at least one alkene linkage. In all these experiments the aqueous layer, if any, was removed and the resulting BSC was distilled at 105°-110° C. at 8 mm Hg. The color of the distilled BSC was measured in 50 ml Nessler tubes by comparison with APHA Color Standards.

TABLE I

| Aqueous Treatment of BSC at 25° C. | |
|---|---|
| Treatment Solution | Color of BSC (APHA) |
| None | >>50 |
| Pure $H_2O$ | 20 |
| Saturated $Cl_2$—$H_2O$ | cloudy, ~15 |
| 10 wt. % $H_2O_2$ | 15 |
| 5 wt. % NaOCl | 5-10 |
| 1 wt. % $KMnO_4$ | <5 |
| 30 wt. % $HNO_3$ | <5 |
| 20 wt. % $Na_2SO_3$ | <5 |
| 1 wt. % $Cl_2$ (based on BSC) + 10 wt. % (based on BSC) of 70 wt. % $HNO_3$ | ~0 |

TABLE II

| Non-Aqueous Treatment of BSC | | | |
|---|---|---|---|
| Treatment Compound | Amount (wt. % BSC) | Temperature (°C.) | Color of BSC (APHA) |
| $(C_2H_5O)_3P$ | 1.0 | 25 | >20 |
| $(CH_3O)_2PHO$ | 2.0 | 25 | 5-10 |
| $(CH_3O)_3P$ | 1.0 | 25 | <5 |
| $(C_6H_5O)_3P$ | 0.5 | 25 | <5 |
| Soybean oil | 1.0 | 25 | <5 |
| Red phosphorus | 0.5 | 145 | 5-10 |
| $NaH_2PO_2 \cdot H_2O$ | 1.0 | 135 | 10-15 |
| 5% Pt/C + air | 0.1 | 145 | <5 |
| $H_2S$ | excess | 130 | 5-10 |
| Corn oil | 1.0 | 25 | <5 |
| Linseed oil | 1.0 | 25 | <5 |

What is claimed is:

1. A process for decolorizing an halide prepared from the reaction of an arylsulfonic acid with a sulfur halide and the corresponding halogen comprising contacting the arylsulfonyl halide with a decolorizing agent selected from the group consisting of an oxidizing agent, a reducing agent, and a compound having at least one alkene linkage, said compound selected from the group consisting of a polybutadiene, a $C_{14}$ to $C_{30}$ alpha-olefin, and an unsaturated vegetable oil.

2. The process of claim 1 wherein the decolorizing agent is an oxidizing agent.

3. The process of claim 2 wherein the oxidizing agent is selected from the group consisting of hydrogen peroxide, sodium hypochlorite, potassium permanganate, chlorine, nitric acid, and air in the presence of platinum on charcoal catalyst.

4. The process of claim 3 wherein the oxidizing agent is a combination of chlorine and nitric acid.

5. The process of claim 1 wherein the decolorizing agent is a reducing agent selected from the group consisting of dimethyl phosphite, trimethyl phosphite, triphenyl phosphite, hydrogen sulfide, sodium hypophosphite and red phosphorus.

6. The process of claim 1 wherein the decolorizing agent is a compound having at least one alkene linkage selected from the group consisting of polybutadiene, $C_{14}$ to $C_{30}$ alpha-olefins, and unsaturated vegetable oils.

7. The process of claim 1 wherein the arylsulfonic acid is benzenesulfonic acid.

8. The process of claim 7 wherein the decolorizing agent is an oxidizing agent.

9. The process of claim 8 wherein the oxidizing agent is selected from the group consisting of hydrogen peroxide, sodium hypochlorite, potassium permanganate, chlorine, nitric acid, and air in the presence of platinum on charcoal catalyst.

10. The process of claim 9 wherein the oxidizing agent is a combination of chlorine and nitric acid.

11. The process of claim 7 wherein the decolorizing agent is a reducing agent selected from the group consisting of dimethyl phosphite, trimethyl phosphite, triphenyl phosphite, hydrogen sulfide, sodium hypophosphite and red phosphorus.

12. The process of claim 7 wherein the decolorizing agent is a compound having at least one alkene linkage selected from the group consisting of polybutadiene, $C_{14}$ to $C_{30}$ alpha-olefins, and unsaturated vegetable oils.

13. A process for decolorizing an arylsulfonyl halide prepared from the reaction of an arylsulfonic acid with a sulfur halide and the corresponding halogen comprising contacting the arylsulfonyl halide with a decolorizing agent selected from the group consisting of an oxidizing agent, a reducing agent, and a compound having at least one alkene linkage, said compound selected from the group consisting of a polybutadiene, a $C_{14}$ to $C_{30}$ alpha-olefin, and an unsaturated vegetable oil and then distilling the arylsulfonyl halide.

14. The process of claim 13 wherein the decolorizing agent is an oxidizing agent.

15. The process of claim 14 wherein the oxidizing agent is selected from the group consisting of hydrogen peroxide, sodium hypochlorite, potassium permanganate, chlorine, nitric acid, and air in the presence of platinum on charcoal catalyst.

16. The process of claim 15 wherein the oxidizing agent is a combination of chlorine and nitric acid.

17. The process of claim 13 wherein the decolorizing agent is a reducing agent selected from the group consisting of dimethyl phosphite, trimethyl phosphite, triphenyl phosphite, hydrogen sulfide, sodium hypophosphite and red phosphorus.

18. The process of claim 13 wherein the decolorizing agent is a compound having at least one alkene linkage selected from the group consisting of polybutadiene, $C_{14}$ to $C_{30}$ alpha-olefins, and unsaturated vegetable oils.

19. The process of claim 13 wherein the arylsulfonic acid is benzenesulfonic acid.

20. The process of claim 19 wherein the decolorizing agent is an oxidizing agent.

21. The process of claim 20 wherein the oxidizing agent is selected from the group consisting of hydrogen peroxide, sodium hypochlorite, potassium permanganate, chlorine, nitric acid, and air in the presence of platinum on charcoal catalyst.

22. The process of claim 21 wherein the oxidizing agent is a combination of chlorine and nitric acid.

23. The process of claim 19 wherein the decolorizing agent is a reducing agent selected from the group consisting of dimethyl phosphite, trimethyl phosphite, triphenyl phosphite, hydrogen sulfide, sodium hypophosphite and red phosphorus.

24. The process of claim 19 wherein the decolorizing agent is a compound having at least one alkene linkage selected from the group consisting of polybutadiene, $C_{14}$ to $C_{30}$ alpha-olefins, and unsaturated vegetable oils.

25. The process of claim 13 wherein the sulfur halide is sulfur monochloride.

26. The process of claim 25 wherein the decolorizing agent is an oxidizing agent.

27. The process of claim 26 wherein the oxidizing agent is selected from the group consisting of hydrogen peroxide, sodium hypochlorite, potassium permanganate, chlorine, nitric acid, and air in the presence of platinum on charcoal catalyst.

28. The process of claim 25 wherein the decolorizing agent is a reducing agent selected from the group consisting of dimethyl phosphite, trimethyl phosphite, triphenyl phosphite, hydrogen sulfide, sodium hypophosphite and red phosphorus.

29. The process of claim 25 wherein the decolorizing agent is a compound having at least one alkene linkage selected from the group consisting of polybutadiene, $C_{14}$ to $C_{30}$ alpha-olefins, and unsaturated vegetable oils.

30. The process of claim 13 wherein the arylsulfonyl halide is benzenesulfonyl chloride.

31. The process of claim 30 wherein the decolorizing agent is an oxidizing agent.

32. The process of claim 31 wherein the oxidizing agent is selected from the group consisting of hydrogen peroxide, sodium hypochlorite, potassium permanganate, chlorine, nitric acid, and air in the presence of platinum on charcoal catalyst.

33. The process of claim 32 wherein the oxidizing agent is a combination of chlorine and nitric acid.

34. The process of claim 30 wherein the decolorizing agent is a reducing agent selected from the group consisting of dimethyl phosphite, trimethyl phosphite, triphenyl phosphite, hydrogen sulfide, sodium hypophosphite and red phosphorus.

35. The process of claim 30 wherein the decolorizing agent is a compound having at least one alkene linkage selected from the group consisting of polybutadiene, $C_{14}$ to $C_{30}$ alpha-olefins, and unsaturated vegetable oils.

* * * * *